United States Patent [19]

Magerlein

[11] 4,032,561

[45] June 28, 1977

[54] 17-PHENYL-18,19,20-TRINOR-CIS-4,5-DIDEHYDRO-PGF$_{1\alpha}$ COMPOUNDS

[75] Inventor: Barney J. Magerlein, Portage, Mich.

[73] Assignee: The Upjohn Company, Kalamazoo, Mich.

[22] Filed: May 27, 1975

[21] Appl. No.: 580,747

[52] U.S. Cl. .................. 260/473 A; 260/520 B
[51] Int. Cl.$^2$ ....................................... C07C 69/76
[58] Field of Search ................ 260/473 A, 520 B

[56] References Cited
FOREIGN PATENTS OR APPLICATIONS 7,306,462  11/1973  Netherlands .................. 260/473
7,501,560  8/1975   Netherlands .................. 260/473 A

*Primary Examiner*—Paul J. Killos
*Attorney, Agent, or Firm*—Robert A. Armitage

[57] ABSTRACT

The disclosure includes novel compounds which differ from the known prostaglandins PGF$_{2\alpha}$, PGF$_{2\beta}$, PGE$_2$, PGA$_2$, and PGB$_2$ in that the carbon-carbon double bond in the carboxylterminated chain of the novel compounds is in the 4,5-position rather than in the 5,6-position, and in that there is a phenyl or substituted phenyl group in the other chain of the novel compounds. These novel compounds are useful for a variety of pharmacological purposes, including abortion, labor induction, and reduction of gastric secretion.

7 Claims, No Drawings

17-PHENYL-18,19,20-TRINOR-CIS-4,5-DIDEHYDRO-PGF$_1$ COMPOUNDS

DESCRIPTION OF THE INVENTION

This invention relates to novel compositions of matter, and to novel processes and novel intermediates useful in making them. More specifically, this invention is concerned with novel optically active organic compounds of the formula

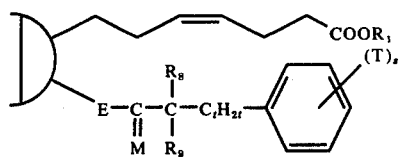

or racemic forms containing one of the above compounds and the enantiomer thereof; wherein D is one of the five carbocyclic moieties:

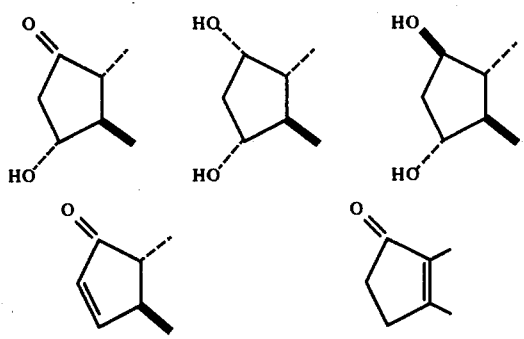

wherein $R_1$ is hydrogen or alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2 or 3 chloro or alkyl of one to 4 carbon atoms, inclusive; wherein M is

wherein $R_2$ is hydrogen methyl, or ethyl; wherein E is trans—CH=CH— or —above-mentioned 2CH —; wherein $R_8$ is hydrogen and $R_9$ is hydrogen, methyl, or fluoro, or wherein $R_8$ and $R_9$ are both methyl or both fluoro, with the proviso that neither of $R_8$ and $R_9$ is methyl when $R_2$ is methyl or ethyl; wherein $C_tH_{2t}$ represents a valence bond or alkylene of one to 9 carbon atoms, inclusive, with one to 6 carbon atoms, inclusive, between —$CR_8R_9$— and the ring; wherein T is alkyl of one to 4 carbon atoms, inclusive, fluoro, chloro, trifluoromethyl, or —$OR_3$, wherein $R_3$ is alkyl of one to 4 carbon atoms, inclusive; and wherein s is zero, one, 2, or 3 with the proviso that not more than 2 T's are other than alkyl; including alkanoates of 2 to 8 carbon atoms, inclusive, and pharmacologically acceptable salts thereof when $R_1$ is hydrogen. Included within the scope of formula 1 are compounds of the formulas:

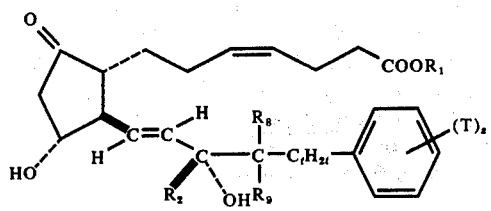

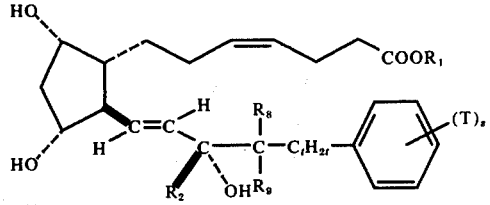

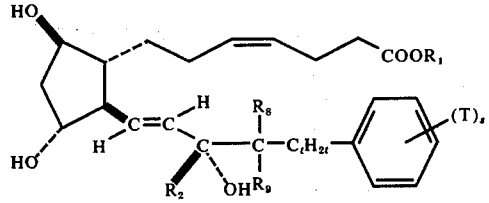

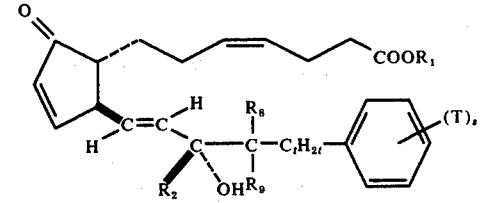

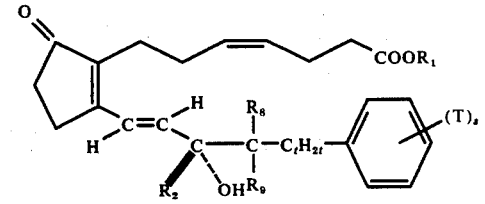

wherein $R_1$, $R_2$, $R_8$, $R_9$, $C_tH_{2t}$, T, and s are as defined above.

Also included within the scope of formula I are compounds of formulas corresponding to formulas II, III, IV, V, and VI above but with one of the following lower side chains

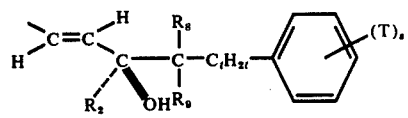

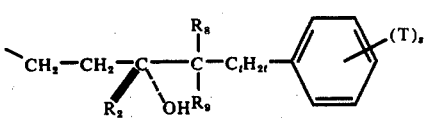

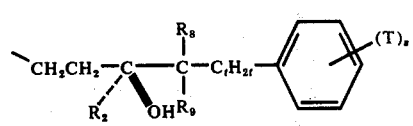

in place of the lower side chain in formulas II, III, IV, V, and VI, wherein also $R_2$, $R_8$, $R_9$, $C_tH_{2t}$, T, and s are as defined above.

This invention is also specifically concerned with novel methods for making these novel compounds of formulas I to IX, inclusive, and with novel chemical intermediates useful in these methods.

The novel compounds of formulas I to IX, inclusive, are related in structure to the substance known as prostanoic acid which has the formula and atom numbering:

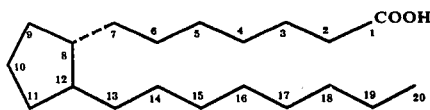

There are known in the art certain compounds named prostaglandins. For example, the compound known as prostaglandin $E_2$ ($PGE_2$) has the formula:

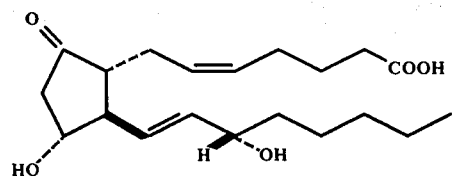

The compound known as prostaglandin $F_{2\alpha}$ ($PGF_{2\alpha}$) has the formula:

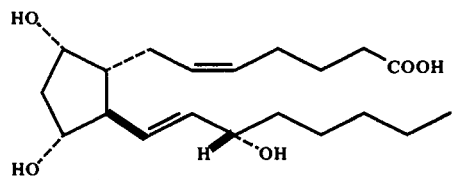

The compound known as prostaglandin $F_{2\beta}$ ($PGB_{2\beta}$) has the formula:

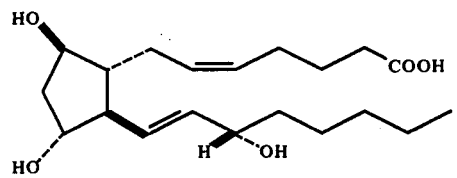

The compound known as prostaglandin $A_2$ ($PGA_2$) has the formula:

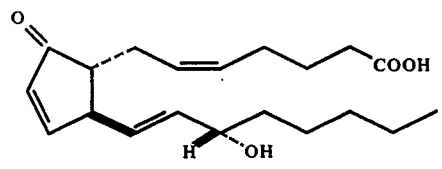

The compound known as prostaglandin $B_2$ ($PGB_2$) has the formula:

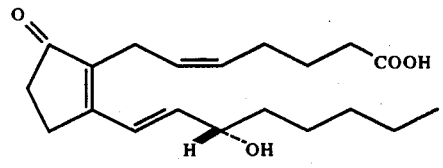

Other compounds which may be considered as analogs of the prostaglandins and which are also related to prostanoic acid are also known in the art. For example, there are known compounds corresponding to the compounds of formulas XI, XII, XIII, and XIV but with a methyl or ethyl group in place of the hydrogen at C-15. See, for example, U.S. Pat. Nos. 3,728,382 and 3,812,179 and German Offenlegungsschrift No. 2,145,600. Also known in the art are compounds corresponding to formulas XI, XII, XIII, and XIV, and also to the above-mentiond alkyl substituted compouns, but with the opposite stereochemical configuraton at C-15. See, for example, U.S. Nos. 3,804,889 and 3,804,890, and German Offenlegungsschrift No. 2,145,600.

Also known in the art are compounds analogous to the known prostaglandins but with no carbon-carbon double bond between C-13 and C-14 as is present, for example, in $PGE_2$ and $PGF_{2\alpha}$. See for example, Hamberg et al., Ann. N.Y. Acad. Sci. 180, 164 (1971), and J. Biol. Chem. 246, 1073 (1971). See also Anggard et al., J. Biol. Chem. 240, 1932 (1965) and Mem. Soc. Endocrinology 14, 107 (1966).

Also known in the art are compounds analogous to the known prostaglandins but with a carbon-carbon double bond between C-4 and C-5 as in the novel formula I- IX compounds of this invention rather than between C-5 and C-6 as in, for example $PGE_2$ and $PGF_{2\alpha}$. See, for example, German Offenlegungsschriften Nos. 2,317,019 and 2,320,552.

Also known in the art are compounds with a phenyl or substituted phenyl ring as part of or in place of part or all of the methyl-terminated chain of $PGE_2$, $PGF_{2\alpha}$, $PGF_{2\beta}$, $PGA_2$, and $PGB_2$. See, for example, German Offenlegungschrift No. 2,154,309.

In the above formulas, as well as in the formulas hereinafter given, broken line attachments to the cyclopentane ring indicate substituents in alpha configuration i.e., below the plane of the cyclopentane ring. Heavy solid line attachments to the cyclopentane ring indicate substituents in beta configuration, i.e., above the plane of the cyclopentane ring. The use of wavy line (~) herein will represent attachment of substituents in either the alpha or beta configuration or attachment in a mixture of alpha and beta configurations.

Molecules of the known prostaglandins (formulas XI to XV), and also molecules of the novel compounds of this invention (formulas I to IX) each have several centers of asymmetry, and each can exist in racemic (optically inactive) form or in either of the two enantiomeric (optically active) forms, i.e., the dextrorotatory and levorotatory forms. As drawn, each of formulas I to XV is intended to represent optically active compounds each with the same absolute configuration as the optically active prostaglandins, for example, $PGE_1$, $PGE_2$, $PGF_{1\alpha}$, $PGF_{2\alpha}$, $PGA_1$, and $PGA_2$ obtained from certain mammalian tissues, for example, sheep vesicular glands, pig lung, and human seminal plasma. See, for example Bergström et al., J. Biol. Chem. 238,3555 (1963), Horton, Experientia 21, 113 (1965), Bergström et al., Pharmacol. Rev. 20, 1 (1968), and references cited in those. The mirror image of each of these formulas represents the other enantiomer of that prostaglandin. The racemic form of a prostaglandin contains equal numbers of both enantiomeric molecules, and one of the above formulas and the mirror image of that formula is needed to represent correctly the corresponding racemic prostaglandin. For convenience hereinafter, use of a "PG" name will mean an optically active form of the compound thereby referred to with the same absolute configuration as $PGE_1$ obtained from mammalian tissues. When reference to racemic forms is intended, the word "racemic" or "dl" will precede the "PG" name.

The configuration of the side chain (C-15) hydroxy shown in formulas XI to XV is sometimes called S although alpha ($\alpha$) is preferred as a designation for this configuration It should be noted that the novel formula I to IX compounds of this invention include not only this S or alpha configuration, shown by attachment of hydroxy to C-15 with a dotted line, but also the opposite configuration at C-15 which is designated variously epi, R, and beta ($\beta$), the last being the preferred designation, shown by attachment to C-15 with a heavy solid line. See Nature, 212, 38 (1966) and Nelson, J. Med. Chem. 17, 911 (1974) for discussion of prostaglandin absolute configuration and nomenclature.

$PGE_2$, $PGF_{2\alpha}$, $PGF_{2\beta}$, $PGA_2$, and $PGB_2$ (formulas XI to XV above), and their esters, acylates, and pharmacologically acceptable salts are extremely potent in causing various biological responses. For that reason, these compounds are useful for pharmacological purposes. See, for example, Bergstrom et al., Pharmacol. Rev. 20, 1 (1968) and references cited therein.

For $PGE_2$ these biological responses include
A. decreasing blood pressure (as measured, for example, in anesthetized, pentolinium-treated rats);
B. stimulating smooth muscle (as shown by tests, for example, on guinea pig ileum, rabbit duodenum, or gerbil colon);
C. effecting lipolytic activity (as shown by antagonism of epinephrine induced release of glycerol from isolated rat fat pads);
D. inhibiting gastric secretion and reducing undesirable gastrointestinal effects from systematic administration of prostaglandin synthetase inhibitors;
E. controlling spasm and facilitating breathing in asthamtic conditions;
F. decongesting nasal passages;
G. decreasing blood platelet adhesion (as shown by platelet to glass adhesiveness) and inhibiting blood platelet aggregation and thrombus formation induced by various physical stimuli (e.g., arterial injury) or chemical stimuli (e.g., ATP, ADP, serotinin, thrombin, and collagen);
H. affecting the reproductive organs of mammals as labor inducers, abortifacients, cervical dilators, regulators of the estrus, and regulators of the menstrual cycle; and
I. accelerating growth of epidermal cells and keratin in animals.

For $PGF_{2\alpha}$ these biological responses include:
A. increasing blood pressure (as measured, for example, in anesthetized, pentolinium-treated rats);
B. stimulating smooth muscle (as shown by tests on guinea pig ileum, rabbit duodenum, or gerbil colon);
C. inhibiting gastric secretion and reducing undesirable gastrointestinal effects from systematic administration of prostaglandin synthetase inhibitors;
D. controlling spasm and facilitating breathing in asthamtic conditions;
E. decongesting nasal passages;
F. decreasing blood platelet adhesion (as shown by platelet to glass adhesiveness) and inhibiting blood platelet aggregation and thrombus formation induced by various physical stimuli (e.g., arterial injury) or chemical stimuli (e.g., ADP, ATP, serotinin, thrombin, and collagen); and
G. affecting the reproductive organs of mammals as labor inducers, abortifacients, cervical dilators, regulators of the estrus, and regulators of the menstrual cycle.

For $PGF_{2\beta}$ these biological responses include:
A. decreasing blood pressure (as measured, for example, in anesthetized, pentolinium-treated rats);
B. stimulating smooth muscle (as shown by tests on guinea pig ileum, rabbit duodenum, or gerbil colon);
C. inhibiting gastric secretion and reducing undesirable gastrointestinal effects from systematic administration of prostaglandin synthetase inhibitors;
D. controlling spasm and facilitating breathing in asthmatic conditions;
E. decongesting nasal passages;
F. decreasing blood platelet adhesion (as shown by platelet to glass adhesiveness) and inhibiting blood platelet aggregation and thrombis formation induced by various physical stimuli (e.g., arterial injury) or chemical stimuli (e.g., ADP, ATP, serotinin, thrombin, and collagen); and
G. affecting the reproductive organs of mammals as labor inducers, abortifacients, cervical dilators, regulators of the estrus, and regulators of the menstrual cycle.

For $PGA_2$ these biological responses include:
A. decreasing blood pressure (as measured, for example, in anesthetized, pentolinium-treated rats);
B. stimulating smooth muscle (as shown by tests on guinea pig ileum, rabbit duodenum, or gerbil colon);
C. inhibiting gastric secretion and reducing undesirable gastrointestinal effects from systematic administration of prostaglandin synthetase inhibitors;
D. controlling spasm and facilitating breathing in asthmataic conditions;
E. decongesting nasal passages; and
F. increasing kidney blood flow.

For $PGB_2$ these biological responses include:
A. stimulating smooth muscle (as shown by tests on guinea pig ileum, rabbit duodenum, or gerbil colon); and
B. accelerating growth of epidermal cells and keratin in animals.

Because of these biological responses, these known prostaglandins are useful to study, prevent, control, or allevaite a wide variety of diseases and undesirable physiological conditions in birds and mammals, including humans, useful domestic animals, pets, and zoological specimens, and in laboratory animals, for example, mice, rats, rabbits, and monkeys.

The prostaglandins so cited as useful hypotensive agents are used to reduce blood pressure in mammals, including man. For this purpose, the compounds are administered by intravenous infusion at the rate about 0.01 to about 50 µg. per kg. of body weight per minute or in single or multiple doses or about 25 to 500 µg. per kg. of body weight total per day.

$PGF_{2\alpha}$ is useful in increasing blood pressure in mammals, including man. Accordingly, this compound is useful in the treatment of shock (hemorrhagic shock, endotoxin shock, cardiogenic shock, surgical shock, or toxic shock). Shock is marked by pallor and clamminess of the skin, decreased blood pressure, feeble and rapid pulse, decreased respiration, restlessness, anxiety, and sometimes unconsciousness. Shock usually follows cases of injury and trauma. Expert and fast emergency measures are required to successfully manage such shock conditions. Accordingly, the prostaglandin, combined with a pharmaceuitcal carrier which adapts the prostaglandin for intramuscular, intravenous, or subcutaneous use, is useful, especially in the early stages of shock where the need to increase blood pressure is a critical problem, for aiding and maintaining adequate blood flow, perfusing the vital organs, and exerting a pressor response by constricting veins and raising blood pressure to normal levels. Accordingly, the prostaglandin is useful in preventing irreversible shock which is characterized by a profound fall in blood pressure, dilation of veins, and venous blood pooling. In the treatment of shock, the prostaglandin is infused as a dose of 0.1 –25 µg./kg./-min. The prostaglandin may advantageously be combined with known vasoconstrictors; such as phenoxybenzamine, norepinephrine, and the like. Further, when used in the treatment of shock the prostaglandin is advantageously combined with steriods (such as, hydrocortisone or methylprednisolone), tranquilizers, and antibiotics (such as lincomycin or clindamycin).

The compounds so cited above as extremely potent in causing stimulation of smooth muscle, are also highly active in potentiating other known smooth stimulators, for example. oxytocic agents, e.g., oxytocin, and the various ergot alkaloids including derivatives and analogs thereof. Therefore, these compounds, for example, are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the prostaglandin is administered by intravenous infusion immediately after abortion or delivery at a dose in the range about 0.01 to about 50 µg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The prostaglandins so cited above as useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract are used for this purpose, by injection or infusion intravenously, subcutaneously, or intramuscularly in an infusion dose range about 0.1 µg. to about 500 µg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

These compounds are also useful in reducing the undesirable gastrointestinal effects resulting from systemic administration of anti-inflammatory prostaglandin synthetase inhibitors, and are used for that purpose by concomitant administration of the prostaglandin and the anti-inflammatory prostaglandin synthetase inhibitor. See Partridge et al., U.S. Pat. No. 3,781,429, for a disclosure that the ulcerogenic effect induced by certain non-steriodal anti-inflammatory agents in rats is inhibited by concomitant oral administration of certain prostaglandins of the E and A series, including $PGE_1$, $PGE_2$, $PGE_3$, 13, 14-dihydro-$PGE_1$, and the corresponding 11-deoxy-PGE and PGA compounds. Prostaglandins are useful, for example, in reducing the undesirable gastrointestinal effects resulting from systemic administration of indomethacin, phenylbutazone, and aspirin. These are substances specifically mentioned in Partridge et al. as non-steriodal anti-inflammatory agents. But these are also known to be prostaglandin synthetase inhibitors.

The anti-inflammatory synthetase inhibitor, for example, indomethacin, aspirin, or phenylbutazone is administered in any of the ways known in the art to alleviate an inflammatory condition, for example, in any dosage regimen and by any of the known routes of systemic administration.

The prostaglandin is administered along with the anti-inflammatory prostaglandin synthetase inhibitor either by the same route of administration or by a differenct route. For example, if the anti-inflammatory substance is being administered orally, the prostaglandin is also administered orally or, alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin is also administered rectally, or, alternatively, orally or, in the case of women, vaginally. It is especially convenient when the administration route is to be the same for both anti-inflammatory substance and prostaglandin, to combine both into a single dosage form.

The dosage regimen for the prostaglandin in accord with this treatment will depend upon a variety of factors, including the type, age, weight, sex and medical condition of the mammal, the nature and dosage regimen of the anti-inflammatory synthetase inhibitor being administered to the mammal, the sensitivity of the particular individual mammal to the particular synthetase inhibitor with regard to gastrointestinal effects, and the particular prostaglandin to be administered. For example, not every human in need of an anti-inflammatory substance experiences the same adverse gastrointestinal effects when taking the substance. The gastrointestinal effects will frequently vary substantially in kind and degree. But it is within the skill of the attending physician or verterinarian to determine that administration of the anti-inflammatory substance is causing undesirable gastrointestinal effects in the human or animal subject and to prescribe an effective amount of the prostaglandin to reduce and then substantially to eliminate those undesirable effects.

The prostaglandins so cited above as useful in the treatment of asthma, are useful, for example, as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia, and emphysema. For these purposes, the compounds are administered in a variety of dosage forms, e.g., orally in the form of tablets, capsules, or liquids; rectally in the form of suppositories; parenterally; subcutaneously; or intramuscularly; with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patent and on the frequency and route of administration. For the above use these prostaglandins can be combined advantageously with other anti-asthmatic agents, such as sympathomimetics (isoproterenol, phenylephrine, epinephrine, etc.); xanthine derivatives (theophylline and aminophylline); and corticosteroids (ACTH and prednisolone). Regarding use of these compounds see M. E. Rosenthale, et al., U. S. Pat. No. 3,644,638.

The prostaglandins so cited above as useful in mammals, including man, as nasal decongestants are used for this purpose, in a dose range of about 10 $\mu$g. to about 10 mg. per ml. of a pharmacologically suitable liquid vehicle or as an aerosol spray, both for topical application.

The prostaglandins so cited above as useful whenever it is desired to inhibit platelet aggregation, to reduce the adhesive character of platelets, and to remove or prevent the formation of thrombi in mammals, including man, rabbits, and rats are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

The prostaglandins so cited above as useful in place of oxytocin to induce labor are used in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 $\mu$g. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

These compounds are further useful for controlling the reproductive cycle in menstruating female mammals, including humans. Menstruating female mammals are animals which are mature enough to menstruate, but not so old that regular menstruation has ceased. For that purpose the prostaglandin is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester the normal mammalian gestation period.

These compounds are further useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by prostaglandins is also useful in operative gynecology such as D and C (Cervical Dilation and Uterine Curettage) where mechanical dilation may cause perforation of the uterus, cervical tears, or infections. It is also useful in diagnostic procedures where dilation is necessary for tissue examination. For these purposes, the prostaglandin is administered locally or systemically.

The prostaglandin, for example, is administered orally or vaginally at doses of about 5 to 50 mg. per treatment of an adult female human, with from one to five treatments per 24 hour period. Alternatively, the prostaglandin is administered intramuscularly or subcutaneously at does of about one to 25 mg. per treatment. The exact dosages for these purposes depend on the age, weight, and condition of the patient or animal.

These compounds are further useful in domestic animals as an abortifacient (especially for feedlot heifers), as an aid to estrus detection, and for regulation or synchronization of estrus. Domestic animals include horses, cattle, sheep, and swine.

The regulation or synchronization of estrus allows for more efficient management of both conception and labor by enabling the herdsman to breed all his females in short predefined intervals. This synchronization results in a higher percentage of live births than the percentage achieved by natural control. The prostaglandin is injected or applied in a feed at doses of 0.1–100 mg. per animal and may be combined with other agents such as steroids. Dosing schedules will depend on the species treated. For example, mares are given the prostaglandin 5–8 days after ovulation and return to estrus. Cattle, are treated at regular intervals over a 3 week period to advantageously bring all into estrus at the same time.

The PGA compounds and derivatives and salts thereof increase the flow of blood in the mammalian kidney, thereby increasing volume and electrolyte content of the urine. For that reason, PGA compounds are useful in managing cases of renal dysfunction, especially those involving blockage of the renal vascular bed. Illustratively, the PGA compounds are useful to alleviate and correct cases of edema resulting, for example, from massive surface burns, and in the management of shock. For these purposes, the PGA compounds are preferably first administered by intravenous injection at a dose in the range 10 to 1000 $\mu$g. per kg. of body weight or by intravenous infusion at a dose in the range 0.1 to 20 $\mu$g. per kg. of body weight per minute until the desired effect is obtained. Subsequent doses are given by intravenous, intramusclar, or subcutaneous injection or infusion in the range 0.05 to 2 mg. per kg. of body weight per day.

The compounds so cited above as promoters and accelerators of the growth of epidermal cells and keratin are used in animals, including humans, useful domestic animals, pets, zoological specimens, and laboratory animals. For this purpose, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For the above purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns and skin loss due to other causes, systemic administration is advantageous, for example, by intravenous injection or infusion, separate or in combinaion with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 $\mu$g. per ml. of the prostaglandin found. Especially for topical use, these prostaglandins are useful in combination with antibiotics, for example, gentamycin, neomycin, polymycin, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

The novel prostaglandin analogs of this invention, namely those of formulae I to IX correspond to the formulae XI to XV to prostaglandins described above, in that these novel prostaglandin analogs exhibit prostaglandin-like biological activity.

Specifically the PGE-type compounds (formula II) of this invention correspond to $PGE_2$, in that these novel PGE-type compounds ar useful for each of the above-described purposes for which $PGE_2$ is used, and are used in the same manner as $PGE_2$ as described above.

The $PGF_\alpha$ -type compounds of this invention (formula III) correspond to $PGF_{2\alpha}$ , in that these novel $PGF_\alpha$ -type compounds are useful for each of the above-described purposes for which $PGF_{2\alpha}$ is used, and are used in the same manner as $PGF_{2\alpha}$ , as described above.

The $PFG_\beta$ -type compounds of this invention (formula IV) correspond to $PGF_{2\beta}$ , in that these novel $PGF_\beta$ -type compounds are useful for each of the above-described purposes for which $PGF_{2\beta}$ is used, and are used in the same manner as $PGF_{2\beta}$ , as described above.

The PGA-type compounds of this invention (formula V) correspond to $PGA_2$, in that these novel PGA-type compounds are useful for each of the above described purposes for which PGA is used, and are used in the same manner as $PGA_2$, as described above.

The PGB-type compounds of this invention (formula VI) correspond to $PGB_2$ described above, in that these PGB-type compounds are useful for each of the above described purposes for which $PGB_2$ is used, and are used in the same manner as $PGB_2$, as described above.

The prostaglandins of formulae XI to XV described above, are all potent in causing multiple biological responses even at low doses. Moreover, for many applications, these prostaglandins have an inconveniently short duration of biological acitivity. In striking contrast, the novel prostaglandin analogs of this invention are substantially more specific with regard to potency in causing prostaglandin-like biological responses, and have a substantially longer duration of biological activity. Accordingly, each of these novel prostaglandin analogs is surprisingly and unexpectedly more useful than one of the corresponding prostaglandins described above for at least one of the pharmacological purposes indicated above for the latter, because it has a different and narrower spectrum of biological potency than the known prostaglandin, and therefore is more specific in its activity and causes smaller and fewer undesired side effects than when the prostaglandin is used for the same purpose. Moreover, because of its prolonged activity, fewer and smaller doses of the novel prostaglandin analog are frequently effective in attaining the desired result.

Another advantage of the novel prostaglandin analogs of this invention, especially the preferred PG analogs defined hereinbelow, compared with the corresponding prostaglandins, is that these novel PG analogs are administered effectively orally, sublingually, intravaginally, buccally, or rectally in those cases wherein the corresponding prostaglandin is effective only by the intravenous, intramuscular, or subcutaneous injection or infusion methods of administration, are advantageous because they facilitate maintaining uniform levels of these compounds in the body with fewer, shorter, or smaller doses, and make possible self-administration by the patient.

Accordingly, the novel formula I to IX prostaglandin analogs of this invention are administered in various ways for various purposes: e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For intravenous injection or infusion, sterile aqueous isotonic solutions are preferred. For that purpose, it is preferred because of increased water solubility that $R_1$ in the novel compounds of this invention be hydrogen or a pharmcologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral sublingual administration. For rectal or vaginal administration, suppositories prepared as known in the art are used. For tissue implants, a sterile tablet or silicone rubber capsule or other object containing or impregnated with the substance is used.

The novel PG analogs of this invention are used for the purposes described above in the free acid form, in ester form, in pharmacologically acceptable salt form. When the ester form is used, the ester is any of those within the above definition of $R_1$ (see formula I above). However, it is preferred that the ester by alkyl of one to 12 carbon atoms, inclusive. Of the alkyl esters, methyl and ethyl are especially preferred for optimum absorption of the compound by the body or experimental animal system, and straight-chain octyl, nonyl, decyl, undecyl, and dodecyl are especially preferred for prolonged activity in the body or experimental animal.

In further respect to esters within the scope of formulae I to IX as above defined, examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof. Examples of cycloaclkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, 2-phenethyl, 1-phenylethyl, 2-phenylpropyl 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Pharmacologically acceptable salts of the novel prostaglandin analogs of this invention useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationinc forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropyamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperzine, and lower-alkyl derivatives thereof, e.g., 1-methylpiperidine, 4-ethylmorpholine, -isopropylpyrrolidine, -isopropyloyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tertamylphenyl)-diethanolamine, galactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The novel PG analogs of this invention are used for the purposes described above in free hydroxy form or also in the form wherein all hydroxy moieties are transformed to lower alkanoate moieties which are acetoxy, propionyloxy, butyryloxy, valeryloxy, hexanoyloxy, heptanoyloxy, octanoyloxy, and branced chain alkanoyloxy isomers of those moieties. Especially preferred among these alkanoates for the above described purposes are the acetoxy compounds. These free hydroxy and alkanoyloxy compounds are used as free acids, as esters, and in salt form all as described above.

In further respect to the novel formula I to IX compounds of this invention, it should be observed that all of the compounds of formulas II to VI have the C-15 hydroxy in alpha (S) configuration, as do $PGE_2$, $PGF_{2\alpha}$, $PGF_{2\beta}$, and $PGB_2$. But it should also be observed that formula I also encompasses compounds wherein the C-15 hydroxy is in beta (R) configuration (see formula VII). These novel 15-β compounds are useful for the same purposes described hereinabove for the corresponding novel 15α-compounds. Generally, however, somewhat higher dose levels are required for the 15-β compound than for corresponding 15α-compounds.

In further respect to the novel formula I to IX compounds of this invention, it should be observed that $C_tH_{2t}$ is defined as a valence bond or alkylene of one to 12 carbon atoms, inclusive, with one to 6 carbon atoms between $-CR_8R_9-$ and the ring, i.e., the phenyl or substituted phenyl ring. By use of this term "valence bond," it is meant that these formulas include compounds wherein said ring is attached directly by a chemical bond (valence bond) to the $-CR_8R_9-$ carbon atom. Further, examples of $C_tH_{2t}$ within the scope of its definition herein are methylene ($-CH_2CH_2-$), ethylene (—CH₂CH₂—), trimethylene, tetramethylene, pentamethylene, and hexamethylene, and also those alkylenes with one or more alkyl substituents on one or more carbon atoms thereof, e.g., —CH(CH₃)—, —C(CH₃)₂—, —CH(CH₂CH₃)—, —CH₂—CH(CH₃)—, —CH(CH₃)—CH(CH₃)—, —CH₂—C(CH₃)₂—, —CH₂—CH(CH₃)—CH₂—, —CH₂—CH₂—CH(CH₂CH₂CH₃)—, —CH(CH₃)—CH(CH₃)—CH₂—, —CH₂—CH₂—Ch₂—C(CH₃)₂—CH₂—, —CH₂ —CH₂—CH₂—CH₂—CH(CH₃)—, —CH₂—CH₂—CH₂—CH₂—C(CH₃)₂—, —CH(CH₃)—CH₂—CH(CH₃)—CH₂—CH₂—CH(CH₃)— and —CH₂—CH₂—CH₂—CH₂—C(CH₃)₂—.

In further respect to the novel formula I to IX compounds of this invention, examples of

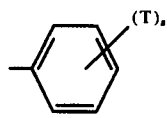

within the scope of its definition herein are phenyl, (o—, m—, or p—)tolyl, (o—, m—, or p—)ethylphenyl, 2-ethyl-o-tolyl, 4-ethyl-o-tolyl, 5-ethyl-m-tolyl, (o—, m—, or p—)propylphenyl, 2-propyl-(o—, m—, p—)tolyl, 4-isopropyl-2,6-xylyl, 3-propyl-4-ethyylphenyl, (2,3,4—, 2,3,5—, 2,3,6—, or 2,4,5—)trimethylphenyl, (o—, m—, or p—)fluorophenyl, 2-fluoro-(o—, m—, or p—) tolyl, 4-fluoro-2,5-xylyl, (2,4-2,5-, 2,6-, 3,4-, or 3,5-)difluorophenyl, (o—, m—, or p—)chlorophenyl, 2-chloro-p-tolyl, (3-, 4-, 5-, or 6-) chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4-chloro-3-fluorophenyl, (3-, or 4-)chloro-2-fluorophenyl, α,α,α-trifluoro-(o—, m—, or p—)tolyl, (o—, m—, or p—)-methoxyphenyl, (o—, , or p—)ethoxyphenyl, (4-, or 5-)chloro-2-methoxyphenyl, and 2,4-dichloro(5- or 6-)methoxyphenyl.

Further, examples of —CR₈R₉— within the scope of its definition herein are —CH₂—, —CHF—, —CF₂, —CH(CH₃)—, and —C(CH₃)₂—. It should be noted however that —CR₈R₉— is —CH(CH₃)— or —C(CH₃)₂— only when R₂ in the moieties R₂́OH and R₂́OH is hydrogen, and not when R₂ is methyl or ethyl.

Although all of the named compounds of formulas I to IX are useful for the above-described purposes, to obtain the optimum combination of biological response specificity, potency, and duration of activity, certain compounds and groups of compounds within the scope of formulas I to IX are preferred.

For example, it is generally preferred that the C-15 hydroxy be in alpha configuration. One exception to this preference is a portion of the novel group of PGE-type compounds corresponding formula II but with the lower side chain shown in formula VII, namely those 15β-PGE-type compounds wherein R₂ is methyl or ethyl. The novel compounds of the 15-methyl-15β-PGE-type or 15-ethyl-15β-PGE-type are at least equally preferred when administered orally for the above-described purposes as the corresponding 15-methyl-15α-PGE-type and 15-ethyl-15α-PGE-type of formula II wherein R₂ is methyl or ethyl.

Another preference for the named compounds of this invention is that they be optically active with the same absolute configuration described above. Another preference is for the novel compounds wherein E in formulas I to IX is trans—CH=CH—. Still another preference is that C₁H₂ₜ be methylene (—CH₂—) or ethylene (—CH₂CH₂—). Still another preference with respect to the aromatic moiety of the formula:

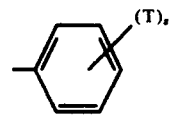

is that s be zero in which case the moiety is phenyl, or that s be one, in which case the moiety is monosubstituted phenyl. Among the substituent within the scope of T as defined above, especially preferred are chloro, fluoro, and trifluoromethyl. Especially preferred is attachment of T to the ring in meta or para position, more especially meta.

With respect to the definition of R₂ as part of M in formula I, the preference is for hydrogen or methyl. With respect to the definition of —CR₈R₉—, the preference is for —CH₂—, —C(CH₃)₂—, and —CHF—.

In choosing preferred compounds within the scope of formulas I to IX, each of the above specific preferences are applied separately and in all of the various combinations. However, there are two groups of compounds which are especially preferred. One of these consists of optically active compounds within the scope of formula I wherein E is trans—CH=CH—, R₁ is hydrogen, methyl, or ethyl, M is

wherein R₂ is hydrogen or methyl, s is zero or one, T when present is chloro, fluoro, or trifluormethyl, R₈ and R₉ are hydrogen, and C₁H₂ₜ is —CH₂— or —CH₂CH₂—, and pharmacologically acceptable salts thereof when R₁ is hydrogen. A second preferred group consists of optically active compounds within the scope of formula I wherein E is tran—CH=CH—, R₁ is hydrogen of methyl, M is

s is zero or one, T when present is chloro, fluoro, or trifluoromethyl, R₈ and R₉ are methyl or R₈ is hydrogen and R₉ is fluoro, and C₁H₂ₜ is —CH₂— or —CH₂CH₂—, and pharmacologically acceptable salts thereof when R₁ is hydrogen.

The novel formula I to IX compounds of this invention are conveniently named on the basis of how they differ from certain of the known prostaglandins. For this purpose, these novel comounds are compared to known prostaglandins of the "one" series (PG₁). Formulas XI to XV hereinabove define known prostaglandins of the "two" series (PG₂). For each of those, there is known a corresponding PG₁. These differ from PG₂ compounds in that in each PG₁ compound, there is no carbon-carbon double bond between C-5 and C-6 as there is in each PG₂ compound. For example, prostaglandin E, (PGE₁) has the formula:

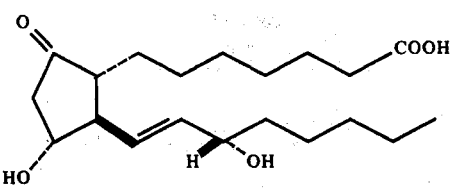

Also known are PGF$_{1\alpha}$, PGF$_{1\beta}$, PGA, and PGB, which correspond to PGF$_{2\alpha}$, PGF$_{2\beta}$, PGA$_2$, and PGB$_x$ (formulas XI to XV, respectively) in the same manner that PGE$_1$ correspond to PGE$_2$.

Now taking a novel PGE-type compound within the scope of formulas I and II and with following formula as an example:

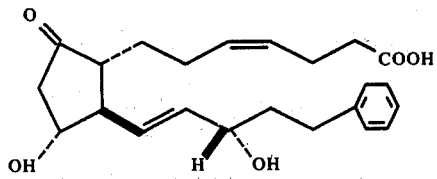

this compound can be given a PGE$_1$-based name. The only difference between this formula XVII and formula XVI (PGE$_1$) are the presence in formula XVII of a cis double bond between C-4 and C-5 (see formula X for numbering system), and the replacement of C-18, C-19, and C-20 of PGE$_1$ (-CH$_2$CH$_2$CH$_3$) with a phenyl moiety. The presence of the cis C-4, C-5 double bond in formula XVII is identified either by the symbol cis-$\Delta^4$ or by the phrase cis-4,5-didehydro, both meaning the presence of a C-4, C-5 double bond in cis configuration and the corresponding absence of a hydrogen from each of the C-4 and C-5 carbons of PGE$_1$. The latter phrase will be used hereinafter. The absence of -CH$_2$CH$_2$CH$_3$ from the lower chain of PGE$_1$ is indicated by the phrase 18,19,20-trinor, "nor" meaning one less CH$_2$ than is present in the reference molecule, here PGE$_1$. The presence of the phenyl moiety attached to C-17 or PGE$_1$ is indicated by the phrase 17-phenyl. Thus, the name for the compound of formula XVII is cis-4,5-didehydro-17-phenyl-18,19,20-trinor-PGE$_1$.

Use of PGE$_1$ in this name indicates that all other structural and stereochemical aspects of PGE$_1$ (formula XIV) are present in the compound of formula XVII.

Another example of this naming system is the novel compound of the formula:

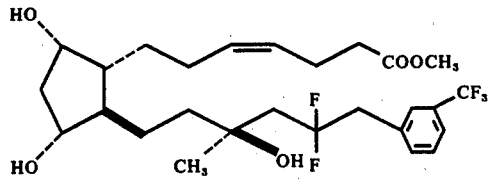

This is a compound within the scope of formulas I and the combination of formulas III and IX, and is named as related to PGF$_{1\alpha}$, which has the formula:

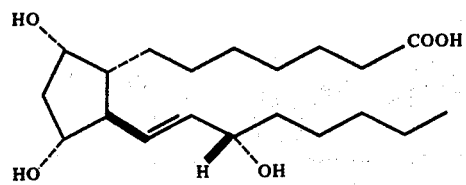

The name of the compound of formula XVIII then is cis-4,5-didehydro-13,14-dihydro-15-methyl-15$\beta$-16,16-difluoro-18-(m-trifluoromethyl)-19,20-dinor-PGF$_{1\alpha}$ methyl ester.

The novel formula I to IX compounds of this invention are prepared by the methods and procedures set forth in Charts A, B, C, and D. With respect to these charts and the discussion which follows, the following definitions obtain:

R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive.

R$_2$ is hydrogen, methyl, or ethyl.

R$_3$ and R$_4$ are alkyl of one to 4 carbon atoms, inclusive.

R$_5$ is R$_1$ except H or the silyl blocking group (A)$_3$—Si—.

CHART A

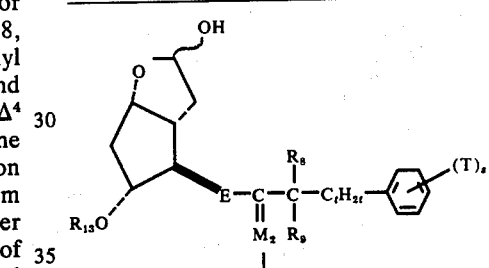

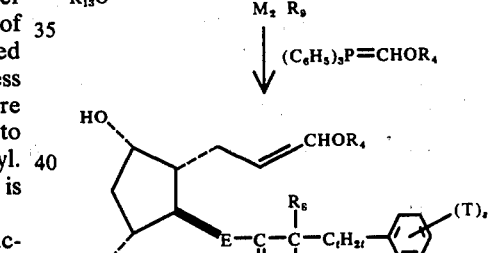

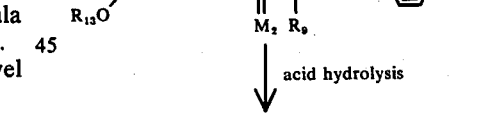

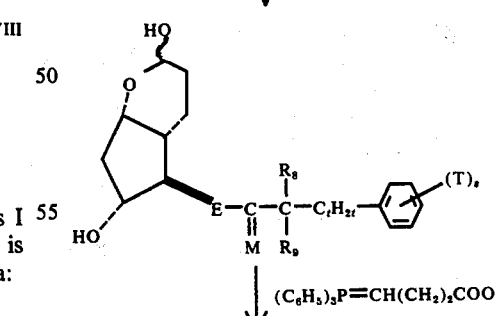

CHART B
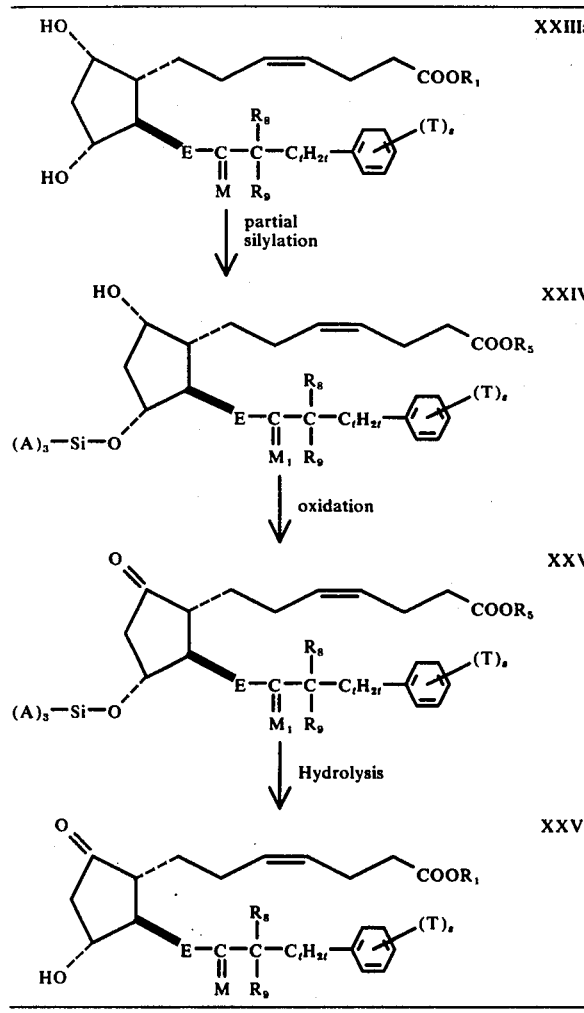
CHART C
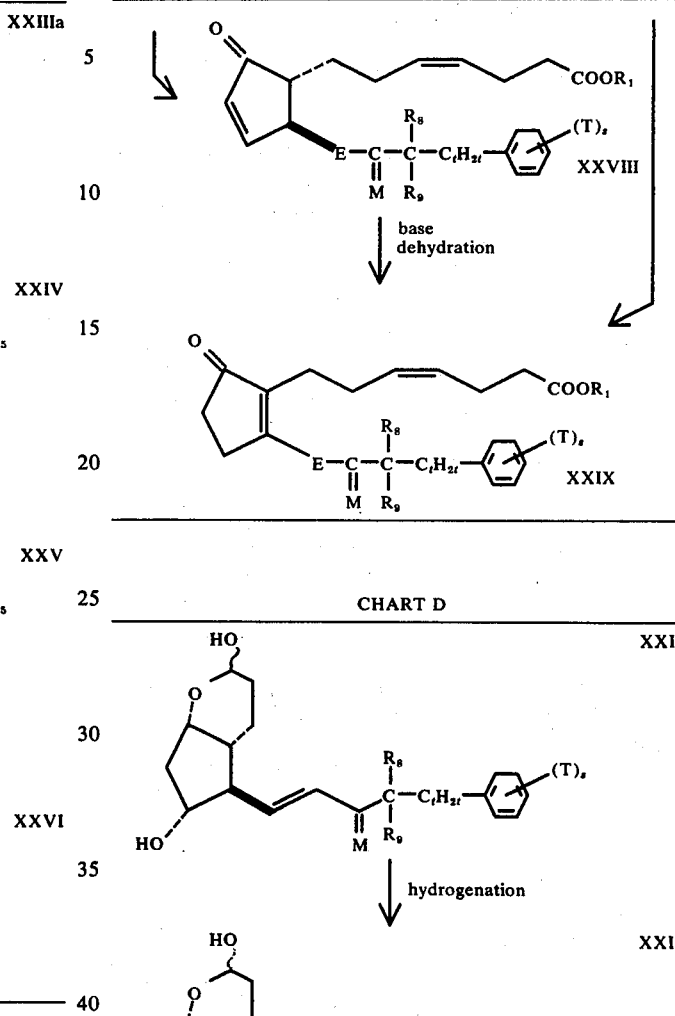
CHART C
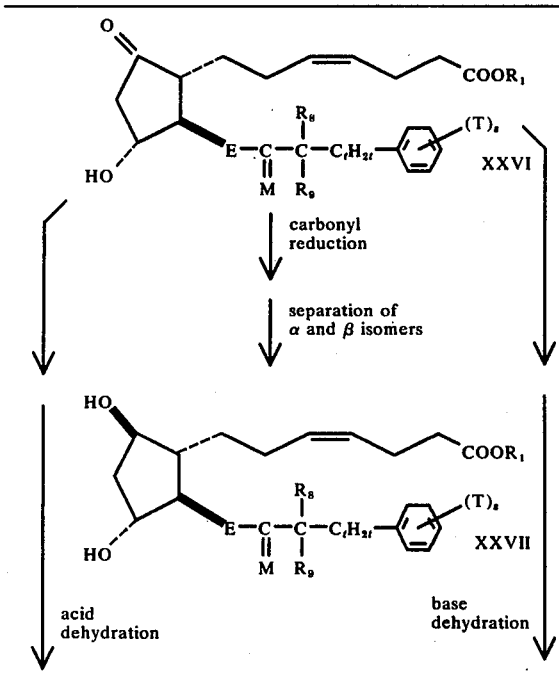
CHART D
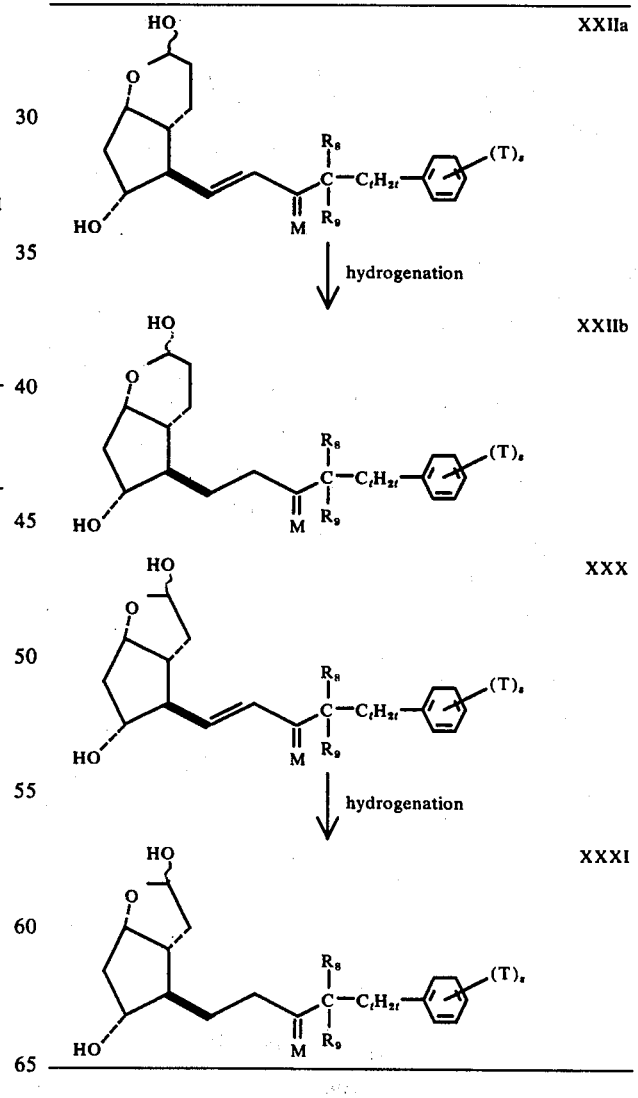
$R_8$ is hydrogen when $R_9$ is hydrogen, methyl, or fluoro, or methyl when $R_9$ is methyl, or fluoro when $R_9$ is fluoro, provided that neither of $R_8$ and $R_9$ are methyl when $R_2$ is methyl.

$R_{13}$ is a removable blocking group.

A is alkyl of one to 4 carbon atoms, inclusive, aralkyl of 7 to 12 carbon atoms, inclusive, phenyl, or phenyl substituted with one or 2 fluoro, chloro, or alkyl of one to 4 carbon atoms, inclusive, the various A's in (a)-$_3$—Si— being the same or different.

E is trans-CH=CH— or —$CH_2CH_2$—.

$C_tH_{2t}$ represents a valence bond or alkylene of one to 9 carbon atoms with one to 6 carbon atoms between —$CR_8R_9$—and the ring.

$C_6H_5$ is phenyl.

M is $R_2^{\sim}$OH or $R_2^{\sim}$OH.

$M_1$ is $R_2^{\sim}$O-Si-(a)$_3$ or $R_2^{\sim}$O-Si-(A)$_3$.

$M_2$ is $R_2^{\sim}OR_{13}$ or $R_2^{\sim}OR_{13}$.

s is zero, one, 2, or 3.

T is alkyl of one to 4 carbon atoms, inclusive, fluoro, chloro, trifluoromethyl, or —$OR_3$, no more than 2 T's being other than alkyl.

The ~ indicates attachment of hydroxy to a ring in alpha or beta configuration.

To extent that the above symbols have already been defined elsewhere in the specification and the claims, the definitions given hereinabove are the same as given elsewhere.

As will be apparent from charts A, B, C, and D, the initial reactants leading to the production of the novel formula I to IX compounds of this invention are the compounds of formula XX at the top of Chart A. As shown in Chart A, these reactants lead through intermediates of formulas XXI and XXII to the product of formula XXII, which are novel PGF$\alpha$ -type compunds of formula III or of the combinations of formulas III and VII (15$\beta$-PGF$_\alpha$ -type compounds), of formulas III and VIII (13,14-dihydro-PGF$_\alpha$ -type compounds), and of formulas III and IX (13,14-dihydro-15$\beta$-PGF$_\alpha$ -type compounds) wherein $R_1$ is hydrogen. When it is desired that $R_1$ be other than hydrogen as defined above, this formula XXIII products are esterified by methods known in the art as explained hereinafter.

Referring now to Chart B, initial reactants XXIIIa are the same as products XXIII in Chart A except that reactants XXIIIa consist of free acids XXIII and also all of the esters of XXIII within the scope of $R_1$ as above defined. Chart B shows the transformation of XXIIIa through intermediates XXIV and XXV to products of formula XXVI, which are novel PGE-type compounds of formula II or of the combination of formulas II and VII (15$\beta$-PGE-type compounds), of formulas II and VIII (13,14-dihydro-PGE-type compounds), and of formulas II and IX (13,14-dihydro-15$\beta$-PGE-type compounds.

Referring now to Chart C, initial reactants XXVI are, of course, the same as the novel formula XXVI PGE-type products of Chart B. As shown in Chart C, these PGE-type compounds are used as reactants to produce products XXVII, XXVIII, and XXIX. The products of formula XXVII are novel PGF$\beta$ -type compounds of formula IV or of the combination of formulas IV and VII (15$\beta$-PGF$\beta$ -type compounds, of formulas IV and VIII (13,14-dihydro-PGF$\beta$ -type compounds) and of formulas IV and IX (13,14-dihydro-15$\beta$-PGF$\beta$ -type compounds). The products of formula XXVIII are novel PGA-type comounds of formula V or of the combination of formulas V and VII (15$\beta$-PGA-type compounds), of formulas V and VIII (13,14-dihydro-PGA-type compounds), and of formulas V and IX (13,14-dihydro-15$\beta$-PGA-type compounds). The products of formula XXIX are novel PGB-type compounds of formula VI and the combination of formulas VI and VII (15$\beta$-PGB-type compounds, of formulas VI and VIII (13,14-dihydro-PGB-type compounds), and of formulas VI and IX (13,14-dihydro-15$\beta$-PGB-type compounds).

Referring back to Chart A, the initial reactants of formula XX are known in the art or are prepared by methods known in the art. Seen German Offenlegungsschrift 2,423,155. See also German Offenlegungsschrift Nos. 2,154,309 which discloses numerous organic halides within the scope of the formula:

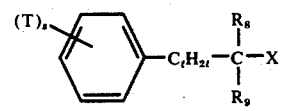

wherein $R_8$, $R_9$, T, s, and $C_tH_{2t}$ are as defined above and X is chloro, bromo, and iodo. The halogen in these is readily replaced with carboxy by methods known in the art, and these carboxylic acids are used in simple ester form as described in German Offenlegugsschrift No. 2,423,155 to prepare the corresponding dimethyl 2-oxoalkylphosphonates used to prepare said formula XX reactants. See, for example, Table I in German Offenlegungsschrift No. 2,154,309 and Preparation 11 in German Offenlegungsschrift No. 2,423,155. Other dimethyl 2-oxoalkylphosphonates are also made in the same manner from other carboxylic acids of the formula:

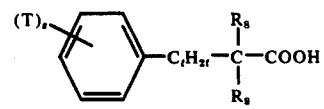

especially those wherein $R_8$ and/or $R_9$ are fluoro or methyl by methods known in the art.

It will be observed in said German Offenlegungsschrift No. 2,423,155 that $R_{13}$ is defined as a "blocking group," and that numerous suitable blocking groups are described therein. These blocking groups are chosen so as to be easily removable by mild acid hydrolysis when a blocking group is no longer needed. It will be observed in Chart A that this occurs during the transformation of XXI to XXII. An especially preferred removably blocking group is tetrahydropyranyl (THP).

Referring again to Chart A, the transformation of initial reactants XX to intermediates XXI, the transformation of XXI to intermediates XXII, and the transformation of XXII to PFG$_\alpha$ -type products XXIII are all carried out as described in German Offenlegungsschriften Nos. 2,317,019 and 2,320,552. These publications disclose this same reaction sequence applied to reactants similar in structure to reactants XX except that the initial reactants, the intermediates, and the PGF$_\alpha$ -type products described in these publications do not have a phenyl or substituted phenyl moiety in the chain attached to the cyclopentane ring.

When a formula XX reactant wherein $R_2$ in M is methyl or ethyl is to be used these are prepared as described in Chart E of German Offenlegungsschrift No. 2,423,155.

When a formula XXIII product wherein E is -$CH_2CH_2$-is desired, the corresponding initial reactant XX, preferably with free hydroxy groups rather than with blocked groups $R_{1\,3}O—$, wherein E is trans—CH=CH— is hydrogenated. Alternatively, intermediate XXII wherein E is tran—CH=CH— is hydrogenated. Both of these hydrogenations transform trans—CH=CH— to —CH$_2$CH$_2$—. These hydrogenations are outlined in Chart D, wherein XXIIa is the same as XXII when E is trans—CH=CH—, and wherein XXIIb is the same as XXII when E is —CH$_2$CH$_2$—. Also in Chart D, XXX and XXXI are the same as XX except that both $R_{1\,3}O$ moieties are HO, and in XXX, E is trans—CH=CH—, while in XXXI, E is —CH$_2$CH$_2$—. Similar hydrogenations are disclosed in German Offenlegungsschrift No. 2,317,019. See Chart G therein. Preferably, the hydrogenation is done catalytically, for example, in the presence of palladium on charcoal or platinum oxide, at about 25°C. and at relataively low hydrogen pressure, e.g., about one to 3 atmospheres of pressure.

Chart A shows the transformation of intermediates XXI to intermediats XXII in a single hydrolysis step. This is in accord with the general procedures described in German Offenlegungsschriften Nos. 2,317,019 and 2,320,552.

It has now been discovered that an improved procedure for transforming XXI to XXII comprises hydrolysis of enol ether XXI in the presence of methanol and under mild acid conditions (pH 2 buffer) so that a δ - lactol methyl ether (~OCH$_3$ rather than ~OH) is formed and isolated. This δ - lactol methyl ether is then hydrolysed under slightly stronger acid conditions (pH 1 aqueous buffer), to the desired formula XXII δ - lactol intermediate. This improved procedure is exemplified below.

Referring now to Chart B, the series of reaction shown therein is intended to transform novel PGF$_\alpha$ - type products from Chart A and their esters to corresponding novel PGE-type products of formula XXVI (same as formula III plus combination of formulas III and VII), The initial reactants XXIIIa in Chart B are either the free acid PGF$_\alpha$ -type products shown as formula XXIII in Chart A, or any of the various esters thereof within the scope of $R_1$ as above defined. The process sequence shown in Chart B involves partial silylation of the free hydroxy groups of C-11 and C-15, leaving the C-9 hydroxy. If $R_1$ in Chart B reactants XXIIIa is hydrogen, the free —COOH is also usually silylated, at least in part. Then, the partially silylated intermediates XXIV are oxidized to transform their C-9 hydroxy to oxo, thereby producing intermediates XXV. The silyl groups from intermediate XXV are then removed to produce the novel PGE-type products XXVI.

When $R_2$ in M of initial reactants XXIIIa is methyl or ethyl, the hydroxy of M may not be silylated since tertiary hydroxy is usually less reactive than secondary hydroxy toward many silylating reagents. But this is not important, since tertiary hydroxy is usually not oxidized or otherwise altered by most reagents used to oxidize a secondary hydroxy (C-9) to oxo.

For this silylation, any of the silylating reagents known in the art for introduction of protective silyl groupings is used. An especially preferred group of reagents, however, is that which will introduce a silyl moiety of the formula —Si—(A)$_3$ wherein A is as defined above. These reagents are known in the art.

The entire reaction sequence outlined in Chart A has already been used for the transformation of other PGF -type compounds to corresponding PGE-type compounds. See, for example, Chart B of German Offenlegungsschrift No. 2,320,552 and Chart C of German Offenlegungsschrift No. 2,317,019. The transformation shown in Chart B herein are carried out by the processes disclosed in those two German Offenlegungsschriften.

Referring now to Chart C, this discloses processes for the transformation of the novel formula XXVI PGE-type products of Chart B to the corresponding novel products of the PGF$_\beta$ -type (formula XXVII), the PGA-type (formula XXVIII), and the PGB-type (formula XXIX). Each of these types of transformations are already known in the art for the transformation of other PGE-type compounds to corresponding PGF$_\beta$ -type, PGA-type, and PGB-type compounds. See, for example, German Offenlegungsschriften Nos. 2,317,019, 2,320,552, and 2,423,155. The transformations shown in Chart C herein are carried out as for the same types of transformations disclosed in those publications.

Esters of the novel formula I to IX compounds of this invention within the scope of $R_1$ as above defined, alkanoates involving all free hydroxy groups, and pharmacologically acceptable salts of the free acid forms of those novel formula I to IX compounds are also made by methods described in the art for making esters, alkanoates, and salts of other known PGE-type, PGF$_\alpha$ -type, PGF$_\alpha$ -type, PGA-type, and PGB-type compounds. See, for example, German Offenlegungsschriften Nos. 2,154,309, 2,317,019, 2,320,552, and 2,423,155.

The invention can be more fully understood by the following examples:

Infrared absorption is measured on a Perkin-Elmer Model 421 infrared spectrophotometer, using undiluted liquid films.

Nuclear magnetic resonance (NMR) spectra are recorded on a Varian A-60 spectrophotometer on deuterochloroform solutions with tetramethylsilane as an internal standard.

"Brine" herein refers to an aqueous saturated sodium chloride solution.

"Skellysolve B" is a mixture of isomeric hexanes.

EXAMPLE 1 cis-4,5-didehydro-17-phenyl-18,19,20-trinor-PGF$_{1\alpha}$ and its Methyl Ester A. Sodium hydride dispersion (8.0 g., 57% sodium hydride, washed with anhydrous hexane to remove mineral oil) and 150 ml. of anhydrous dimethyl sulfoxide are stirred together at 65°–70° C. under a dry nitrogen atmosphere until a clear solution is obtained (about 2 hours). This solution is cooled to 15° C., and (methoxymethyl)-triphenylphosphonium bromide (65 g.) is added as a solid with vigorous stirring. After 15 minutes with stirring at 15° C., a solution of a δ-lactol (35.8 g.) of formula XX wherein M$_2$ is H̃OTHP, R$_8$ and R$_9$ are hydrogen, R$_{13}$ is THP, E is trans-CH×CH=CH—, C$_t$H$_{2t}$ is —CH$_2$—, and s is zero, in 100 ml. of dimethyl sulfoxide is added dropwise. Stirring at 15° C. is continued for 2 hours, the reaction being monitored by shaking an aliquot with water and diethyl ether, and tlc of the ether layer on silica gel with acetone-Skellysolve B (1:4 by volume). Water (650 ml.) is then added slowly with stirring and external cooling with a mixture of ice and water. The resulting mixture is stirred for 30 minutes, and then poured into 350 ml. of water. This mixture is saturated with sodium chloride and then extracted five times with 500-ml. portions of diethyl ether. The combined extracts are washed twice with 150-ml. portions of brine, dried with anhydrous magnesium sulfate, and evaporated under reduced pressure to give 71 g. of a dark brown oil. This oil is dissolved in several volumes of diethyl ether and the solution is cooled to about $-15°$ C. and maintained at that temperature until a precipitate ceases forming. This precipitate is filtered and washed with diethyl ether, and the filtrate and washings are combined and evaporated under reduced pressure. The resulting oil is dissolved in benzene, and benzene is distilled from the solution until no more water appears in the distillate. The remaining benzene is evaporated, and the oil is again azeotroped with benzene. Evaporation of the remaining benzene under reduced pressure gives 53 g. of an oil which is chromotographed on 3 kg. of silica gel, packing as a slurry with acetone-Skellysolve B (15:85 by volume), and eluting first with 2 l. of the same solvent mixture and then with acetone-Skellysolve B (2:8 by volume), collecting seven 1-l. fractions and then 350-ml. fractions. Fractions 18–27 are combined and evaporated under reduced pressure to give 19.17 g. of a cis-trans mixture of an enol ether product of formula XXI wherein $M_2$ is $H^*OTHP$, $R_4$ is methyl, $R_8$ and $R_9$ are hydrogen, $R_{13}$ is THP, $C_tH_{2t}$ is $-CH_2-$, and s is zero. A sample of substance in fraction 19 which is the cis isomer shows infrared absorption at 3500, 1600, 1495, and 975 cm$^{-1}$, and NMR peaks at 7.22 (singlet), 6.34 (doublet), 5.56 (multiplet), 4.72 (multiplet), and 2.58 (singlet) δ.

B. An aqueous pH 2 buffer solution (400 ml.; made in ratio of 25 ml. 0.2 M potassium chloride and 6.5 ml. 0.2 M hydrochloric acid) is added to a solution of the enol ether product (cis-trans mixture) of part A (19.0 g.) in 1 l. of methanol at about 25° C. After 16.5 hours, the reaction is complete as shown by tlc evidence in chloroform-methanol (9:1) on silica gel. About 75% of the methanol is then removed under reduced pressure, and 300 ml. of brine is added to the concentrate. This solution is extracted with four 350-ml. portions of chloroform, and the combined extracts are washed with two 100-ml. portions of brine, dried with anhydrous magnesium sulfate, and evaporated under reduced pressure to give as a pale yellow oil, the methyl ether of the δ-lactol of formula XXII wherein E is trans—CH=CH—, M is $H^*·OH$, $R_8$ and $R_9$ are hydrogen, $C_tH_{2t}$ is —CH$_2$—, and s is zero; infrared absorption at 3390, 1665, 1600, 1495, 975, 750, and 700 cm$^{-1}$; NMR peaks at 7.20 (singlet), 5.53 (multiplet), 4.97 (multiplet), and 3.45 and 3.37 (singlets) δ.

C. An aqueous pH 1 buffer solution (500 ml.; made in ratio of 25 ml. 0.2 M potassium chloride and 67 ml. 0.2 M hydrochloric acid) is added to a solution of the δ-lactol methyl ether product of part B (12.4 g.) in 500 ml. of tetrahydrofuran at about 25° C. The reaction is monitored by tlc as in part B. After 20 hours at about 25° C., an additional 250 ml. of the same pH 1 buffer is added, and the solution maintained at 25° C. for an additional 25 hours. Then, the solution is saturated with sodium chloride. The lighter non-aqueous layer is separated, and the heavier aqueous layer is extracted four times with dichloromethane. The extracts are combined with said non-aqueous layer, and this combination is washed with brine until successive washings are neutral. The brine washings are combined and extracted with dichloromethane, this extract being added to the other dichloromethane extracts. The combined organic solutions are then dried with anhydrous magnesium sulfate and evaporated under reduced pressure to give in the form of a yellow oil (14 g.) a δ-lactol of formula XXII wherein E is trans-CH=CH—, M is $H^*·OH$, $R_8$ and $R_9$ are hydrogen, $C_tH_{2t}$ is —CH$_2$—, and s is zero; NMR peaks at 7.21 (multiplet) and 5.51 (multiplet) δ.

D. Sodium hydride dispersion (6.32 g., 57% sodium hydride, washed with anhydrous hexane to remove mineral oil) and 100 ml. of anhydrous dimethyl sulfoxide are stirred together at 60°–70° C. under dry nitrogen until a clear solution is obtained (about 1.5 hours). This solution is cooled to 20° C., and 3-carboxypropyl-triphenylphosphonium bromide (32.2 g.) is added as a solid with vigorous stirring. The resulting mixture is then stirred one hour at about 25° C. To this mixture is added a solution of the δ-lactol product of part C (3.73 g.) in 30 ml. of dimethyl sulfoxide. This mixture is stirred about 15 hours at 25° C. Then, the mixture is diluted with about three volumes of benzene, and the mixture is transferred to a separatory funnel. Ice is added to the mixture which is then acidified with 10% aqueous potassium hydrogen sulfate solution added in portions with shaking. The upper organic layer is separated, and the aqueous layer is washed twice with benzene. During this extraction, a crystalline precipitate forms and is separated by filtration and discarded. Said upper organic layer and the benzene washings are combined, dried with anhydrous magnesium sulfate, and evaporated under reduced pressure. The resulting residue is dissolved in diethyl ether, and this solution is extracted once with 1 N aqueous sodium hydroxide solution and twice with water. The combined aqueous extracts are acidifed in the presence of diethyl ether with 10% aqueous potassium hydrogen sulfate solution to pH less than 3, and then extracted repeatedly with diethyl ether. The combined extracts are washed with brine, dried with anhydrous magnesium sulfate, and evaporated under reduced pressure to give 4.64 g. of residue A. Then, all previous aqueous layers are combined, saturated with sodiuum chloride, and extracted repeatedly with dichloromethane. The dichloromethane extracts are combined, dried with anhydrous magnesium sulfate, and evaporated under reduced pressure to give 6.92 g. of residue B. Residues A and B are combined and chromatographed on 1 kg. of acid-washed silica gel (Mallinkrodt CC4), packing as a slurry with benzene-ethyl acetate (4:6 by volume), and eluting with the same solvent mixture, collecting 42 150-ml. fractions, 54 250-ml. fractions, and then 2-l. fractions, changing the eluting mixture to benzene-ethyl acetate (25:75 by volume) at fraction 47 and to 100% ethyl acetate at fraction 96 for a total of 4 l., and then eluting with 2 l. of methanol. Fractions 61–98 are combined and evaporated under reduced pressure. The residue is slurried with acetone, and the slurry is filtered. The acetone filtrate is evaporated under reduced pressure, and the residue is dissolved in a mixture of dichloromethane and diethyl ether (1:1 by volume). Excess diazomethane in diethyl ether is added to this solution, and the mixture is evaporated under reduced pressure after methyl ester formation is complete to give 4.9 g. of a yellow oil which is chromatographed on 500 g. of silica gel, packing as a slurry with acetone-dichloromethane (4:6 by volume), and eluting with 1 l. of acetonedichloromethane (45.55 by volume), followed by acetonedichloromethane (1:1 by volume), collecting 110-ml. fractions. Fractions 26-56 are combined and evaporated under reduced pressure to give 2.36 g. of residue, which is chromatographed on 230 g. of silica gel, dry packing after deactivation with 100 ml. of methanol-chloroform (7.5:92.5 by volume), and eluting with the same solvent mixture, collecting 60-ml. fractions. Fraction 8 is evaporated under reduced pressure, and the residue (0.69 g.) is rechromatographed on 80 g. of silica gel, dry packing after deactivation with 80 ml. of methanol-chloroform (5:95 by volume), and eluting with the same solvent mixture, collecting 25-ml. fractions. Fractions 13-25 are combined with fractions 9-15 from the preceeding chromatographic column, and these combined fractions are evaporated under reduced pressure to give 1.82 g. of cis-4,5-didehydro-17-phenyl-18,19,20-trinor-$PGF_{1\alpha}$ methyl ester; infrared absorption at 3360, 1735, 1600, 1495, 970, 750, and 700 cm$^{-1}$; NMR peaks at 7.18 (singlet), 5.42 (multiplet), and 3.61 (singlet) δ. This methyl ester is saponified with aqueous ethanolic sodium hydroxide to give cis-4,5-didehydro-17-phenyl-18,19,20-trinor-$PGF_{1\alpha}$ in free acid form.

EXAMPLE 2 cis-4,5-didehydro-17-phenyl-18,19,20-trinor-$PGE_1$ and its Methyl Ester

A. N-Trimethylsilyldiethylamine (2.7 ml.) is added to a solution of cis-4,5-didehydro-17-18,19,20-trinor-$PGF_{1\alpha}$ methyl ester (0.306 g.) in 10 ml. of acetone at −20° C. under an atmosphere of dry nitrogen. This mixture is maintained at −20° C., and the reaction is monitored by tlc on silica gel with Skellysolve B-ethyl acetate (1:1 by volume). After about 2.5 hours, the mixture is diluted with 32 ml. of diethyl ether precooled at −78° C. This mixture is added to 50 ml. of half-saturated aqueous sodium bicarbonate solution in a separatory funnel. The resulting mixture is shaken and the organic layer is separated. The aqueous layer is extracted four times with diethyl ether, and these extracts and said organic layer are combined, washed twice with brine, dried with anhydrous sodium sulfate, and evaporated under reduced pressure at 40° C. The residue is azeotroped (as in Example 1, part A) twice with benzene, and then the benzene is evaporated under reduced pressure to give in the form of a pale yellow oil (408 mg.) the disilyl intermediate of formula XXIV wherein A is methyl, E is trans-CH=CH—, $R_5$ is methyl, $R_8$ and $R_9$ are hydrogen, $C_tH_{2t}$ is —CH$_2$—, and s is zero; tlc $R_f$ = 0.66 on silica gel with ethyl acetate-Skellysolve B (1:1 by volume).

B. Pyridine (0.43 ml.) is added with stirring to a solution of dry chromium trioxide (270 mg.) in 11 ml. of dichloromethane at 25° C. under dry nitrogen. The mixture is stirred 2 hours at 25° C., and then cooled to 0° C. A solution of the disilyl intermediate from part A (0.37 mmole) in 1.5 ml. of dichloromethane is added, and the mixture is stirred 10 min. at 0° C. This mixture is then poured onto a 3-inch layer of silica gel in a sintered glass funnel, rinsing reaction vessel walls with additional dichloromethane and adding the rinsings to the silica gel layer. The silica gel layer is then washed with 150 ml. of ethyl acetate. This washing is collected by filtration, and the filtrate is evaporated under reduced pressure. The residue is dissolved in 7 ml. of methanol, and this solution is mixed with a solution containing 3.5 ml. of water and 0.4 ml. of acetic acid. This mixture is stirred 45 min. at 25° C., and is then added to a mixture of ice, 13 ml. of 0.1 M aqueous sodium hydrogen sulfate solution, and 7 ml. of diethyl ether. The total mixture is shaken and the layers separated. The aqueous layer is extracted five times with 7-ml. portions of diethyl ether. These extracts and the organic layer are combined, washed successively with water to pH 5 to 7 in a wash water, with saturated aqueous sodium bicarbonate solution, and with brine, dried with anhydrous sodium sulfate, and evaporated under reduced pressure. The residue is azeotroped twice with benzene (as in Example 1, part A), and then evaporated under reduced pressure at 25° C. to give 116 mg. of an oil. This oil is chromatographed on 12 g. of silica gel, packing as a slurry and eluting with ethyl acetate, collecting 3.5-ml. fractions. Fractions 21-40 are combined and evaporated under reduced pressure to give 55 mg. of cis-4,5-didehydro-17-phenyl-18,19,20-trinor-$PGE_1$ methyl ester; infrared absorption at 3400, 3020, 3000, 1735, 970, 750, and 700 cm$^{-1}$; NMR peaks at 7.21 (singlet), 5.66 and 5.32 (both multiplets), and 3.61 (singlet) δ.

Following the above procedures, with appropriate modifications in isolation procedures, cis-4,5-didehydro-17-phenyl-18,19,20-trinor-$PGF_{1\alpha}$ free acid is transformed to cis-4,5-didehydro-17-phenyl-18,19,20-trinor-$PGE_1$ in free acid form. Alternatively, the cis-4,5-didehydro-17-phenyl-18,19,20-trinor-$PGE_1$ methyl ester prepared as above is hydrolyzed enzymatically by the procedure set forth in Example 28 of German Offenlegungsschrift No. 2,423,155.

EXAMPLE 3 cis-4,5-Didehydro-17-phenyl-18,19,20-trinor-$PGA_1$

A solution of cis-4,5-didehydro-17-phenyl-18,19,20-trinor-$PGE_1$ (300 mg.), 4 ml. of tetrahydrofuran, and 4 ml. of 0.5 N hydrochloric acid is left standing at 25° C. for five days. Brine and dichloromethane-diethyl ether (1:3) are added and the mixture is stirred. The organic layer is separated, dried and concentrated. The residue is dissolved in ether and the solution is extracted with saturated aqueous sodium bicarbonate. The aqueous phase is acidified with dilute hydrochloric acid and extracted with dichloromethane. This extract is dried and concentrated to yield cis-4,5-didehydro-17-phenyl-18,19,20-trinor-$PGA_1$.

EXAMPLE 4 cis-4,5-Didehydro-17-phenyl-18,19,20-trinor-$PGB_1$

A solution of cis-4,5-didehydro-17-phenyl-18,19,20-trinor-$PGE_1$ (200 mg.) in 100 ml. of 50% aqueous ethanol containing about one gram of potassium hydroxide is kept at 25° C. for 10 hours under nitrogen. Then, the solution is cooled to 10° C. and neutralized by addition of 3 N. hydrochloric acid at 10° C. The resulting solution is extracted repeatedly with ethyl acetate, and the combined ethyl acetate extracts are washed with water and then with brine, dried, and concentrated to give cis-4,5-didehydro-17-phenyl-18,19,20-trinor-$PGB_1$.

EXAMPLE 5 cis-4,5-Didehydro-17-phenyl-18,19,20-trinor-$PGF_{1\beta}$ Methyl Ester

A solution of 600 mg. of sodium borohydride in 10 ml. of ice-cold methanol is added to a solution of 1.34 g. of cis-4,5-didehydro-17-phenyl-18,19,20trinor-$PGF_1$ methyl ester in 60 ml. of methanol, and the reaction mixture is stirred at 0° C. for 30 minutes. Acetone (10 ml.) is added and the solution is made slightly acid with dilute acetic acid in methanol. The mixture is concentrated under reduced pressure and the residue is taken up in dichloromethane. The solution is washed with brine, dried over sodium sulfate, and evaporated under reduced pressure to give a residue which is chromatographed over 250 g. of silica gel wet-packed in 8% methanol in dichloromethane and rinsed with 300 ml. of dichloromethane, eluting with 250 ml. of 5%, 500 ml. of 6%, 1000 ml. of 8% and 250 ml. of 10% methanol in dichloromethane, taking 25 ml. fractions. Fractions shown by tlc to contain cis-4,5-didehydro-17-phenyl-18,19,20-trinor-PGF$_{1\alpha}$ are separated from fractions shown to contain the β-isomer, and the latter fractions are combined and evaporated under reduced pressure to give cis-4,5-didehydro-17-phenyl-18,19,20-trinor-PGF$_{1\beta}$ methyl ester.

EXAMPLE 6 cis-4,5-Didehydro-15-methyl-17-phenyl-18,19,20-trinor-PGF$_{1\alpha}$, -PGE$_1$, -PGA$_1$, -PGB$_1$, and -PGF$_{1\beta}$ and their methyl esters Following the procedures of Example 1, but using the γ-lactol of formula XX wherein M$_2$ is CH$_3$ OTHP, R$_8$ and R$_9$ are hydrogen, R$_{13}$ is THP, E is trans—CH=λ CH—, C$_t$H$_{2t}$ is —CH$_2$—, and s is zero in place of the γ-lactol used in Example 1, there is obtained cis-4,5-didehydro-15-methyl-17-phenyl-18,19,20-trinor-PGF$_{1\alpha}$ methyl ester and the free acid thereof. Then, following the procedures of Examples 2, 3, 4, and 5, using the above PGF$_\alpha$ -type compounds, there are obtained cis-4,5-didehydro-15-methyl-17-phenyl-18,19,20-trinor-PGE$_1$ and its methyl ester, cis-4,5-didehydro-15-methyl-17-phenyl-18,19,20-trinor-PGA$_1$, cis-4,5-didehydro-15-methyl-17-phenyl-18,19,20-trinor-PGB$_1$, and cis-4,5-didehydro-15-methyl-17-phenyl-18,19,20-trinor-PGF$_{1\beta}$ and its methyl ester, the methyl esters of the PGA-type and the PGB-type compounds being prepared by reacting each of those free acids with diazomethane.

EXAMPLE 7 cis-4,5-Didehydro-16,16-dimethyl-17-phenyl-18,19,20-trinor-PGF$_{1\alpha}$, -PGE$_1$, -PGA$_1$, -PGB$_1$, and -PGF$_{1\beta}$ and their methyl esters Following the procedure of Example 1 but using the γ-lactol of formula XX wherein M$_2$ is H OTHP, R$_8$ and R$_9$ are methyl, R$_{13}$ is THP, E is trans—CH=CH—, C$_t$H$_{2t}$ is —CH$_2$—, and s is zero in place of the γ-lactol used in Example 1, there is obtained cis-4,5-didehydro-16,16-dimethyl-17-phenyl-18,19,20-trinor-PGF$_{1\alpha}$ methyl ester and the free acid thereof. Then, following the procedures of Examples 2, 3, 4, and 5, using the above PGF$_\alpha$ -type conmpounds, there are obtained cis-4,5-didehydro-16,16-dimethyl-17-phenyl-18,19,20-trinor-PGE$_1$, and its methyl ester, cis-4,5-didehydro-16,16-dimethyl-17-phenyl-18,19,20-trinor-PGA$_1$, cis-4,5-didehydro-16,16-dimethyl-17-phenyl-18,19,20-trinor-PGB$_1$, and cis-4,5-didehydro-16,16-dimethyl-17-phenyl-18,19,20-trinor-PGF$_{1\beta}$ and its methyl ester, the methyl esters of the PGA-type and the PGB-type being prepared by reacting each of those free acids with diazomethane.

EXAMPLE 8 cis-4,5-Didehydro-16-fluoro-17-phenyl-18,19,20-trinor-PGF$_{1\alpha}$, -PGE$_1$, -PGA$_1$, -PGB$_1$, and -PGF$_{1\beta}$ and their methyl esters Following the procedures of Example 1 but using the γ-lactol of formula XX wherein M$_2$ is H OTHP, R$_8$ is hydrogen, R$_9$ is fluoro, R$_{13}$ is THP, E is trans—CH=λ CH—, C$_t$H$_{2t}$ is —CH$_2$—, and s is zero in place of the δ-lactol used in Example 1, there is obtained cis-4,5-didehydro-16-fluoro-17-phenyl-18,19,20-trinor-PGF$_{1\alpha}$ methyl ester and the free acid thereof. Then, following the procedures of Examples 2, 3, 4, and 5, using the above PGF$_\alpha$ -type compounds, there are obtained cis-4,5-didehydro-16-fluoro-17-phenyl-18,19,20-trinor-PGE$_1$ and its methyl ester, cis-4,5-didehydro-16-fluoro-17-phenyl-18,19,20-trinor-PGA$_1$, cis-4,5-didehydro-16-fluoro-17-phenyl-18,19,20-trinor-PGB$_1$, and cis-4,5-didehydro-16-fluoro-17-phenyl-18,19,20-trinor-PGF$_1$ and its methyl esters, the methyl esters of the PGA-type and the PGB-type being prepared by reacting each of those free acids with diazomethane.

EXAMPLE 9 cis-4,5-Didehydro-13,14-dihydro-17-phenyl-18,19,20-trinor-PGF$_{1\alpha}$, -PGE$_1$, -PGA$_1$, -PGB$_1$, and -PGF$_{1\beta}$ and their methyl esters Following the procedures of Example 1, but using the γlactol of formula XX wherein M$_2$ is H OTHP, R$_8$ and R$_9$ are hydrogen, R$_{13}$ is THP, E is —CH$_2$CH$_2$—, C$_t$H$_{2t}$ is —CH$_2$—, and s is zero in place of the γ-lactol used in Example 1, there is obtained cis-4,5-didehydro-13,14-dihydro-17-phenyl-18,19,20-trinor-PGF$_{1\alpha}$ methyl ester and the free acid thereof. Then, following the procedures of Examples 2, 3, 4, and 5, using the above PGF$_\alpha$-type compounds, there are obtained cis-4,5-didehydro-13,14-dihydro-17-phenyl-18,19,20-trinor-PGE$_1$ and its methyl ester, cis-4,5-didehydro-13,14-dihydro-17-phenyl-18,19,20-trinor-PGA$_1$, cis-4,5-didehydro-13,14-dihydro-17-phenyl-18,19,20-trinor-PGB$_1$, and cis-4,5-didehydro-13,14-dihydro-17-phenyl-18,19,20-trinor-PGF$_{1\beta}$ and its methyl esters, the methyl esters of the PGA-type and the PGB-type being prepared by reacting each of those free acids with diazomethane.

Also following the procedures of Examples 1, 2, 3, 4, and 5, each of the γ-lactols within the scope of formula XX which are disclosed in German Offenlegungsschrift No. 2,423,155, for example, in Example 33 thereof, and each of the γ-lactols within the scope of formula XX which are prepared as described above from intermediate halides disclosed in German Offenlegungsschrift No. 2,154,309, for example, in Table 1 thereof, there are obtained corresponding cis-4,5-didehdro-PGE$_1$, -PGF$_{1\alpha}$, -PGF$_{1\beta}$, -PGA$_1$, and -PGB$_1$ type compounds, all within the scope of formulas II, III, IV, V, and VI, respectively. Also, each of those same γ-lactols is hydrogenated to produce corresponding formula XX γ-lactols wherein E is —CH$_2$CH$_2$—, and each of the latter γ-lactols is transformed by the procedures of Examples 1, 2, 3, 4, and 5 to corresponding cis-4,5-didehydro-13,14-dihydro-PGE$_1$, -PGF$_{1\alpha}$, -PGF$_{1\beta}$, -PGA$_1$, and -PGB$_1$ type compounds, all within the scope of formulas II, III, IV, V, and VI, respectively.

I claim:

1. An optically active compound of the formula:

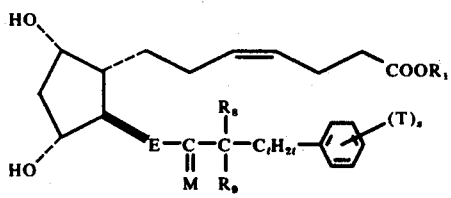

or a racemic form of that compound and the enantiomer thereof, wherein $R_1$ is hydrogen or alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2 or 3 chloro or alkyl of one to 4 carbon atoms, inclusive;

wherein M is $\overset{\frown}{R_2}OH$ or $\overset{\frown}{R_2}OH$, wherein $R_2$ is hydrogen, methyl, or ethyl;

wherein E is trans—CH=CH— or —$CH_2CH_2$—;

wherein $R_8$ is hydrogen and $R_9$ is hydrogen, methyl, or fluoro, or wherein $R_8$ and $R_9$ are both methyl or both fluoro, with the proviso that neither of $R_8$ and $R_9$ is methyl when $R_2$ is methyl or ethyl;

wherein $C_tH_{2t}$ represents a valence bond or alkylene of one to 9 carbon atoms, inclusive, with one to 6 carbon atoms, inclusive, between —$CR_8R_9$— and the ring;

wherein T is alkyl of one to 4 carbon atoms, inclusive, fluoro, chloro, trifluoromethyl, or —$OR_3$, wherein $R_3$ is alkyl of one to 4 carbon atoms, inclusive and wherein s is zero, one, 2, or 3 with the proviso that not more than 2 T's are other than alkyl; including alkanoates of 2 to 8 carbon atoms, inclusive, and pharmacologically acceptable salts thereof when $R_1$ is hydrogen.

2. An optically active compound according to claim 1 wherein E is trans—CH=CH—, $R_1$ is hydrogen, methyl, or ethyl, M is $\overset{\frown}{R_2}OH$ wherein $R_2$ is hydrogen or methyl, s is zero or one, T when present is chloro, fluoro, or trifluoromethyl, $R_8$ and $R_9$ are hydrogen, and $C_tH_{2t}$ is —$CH_2$— or —$CH_2CH_2$—, and pharmacologically acceptable salts thereof when $R_1$ is hydrogen.

3. An optically active compound according to claim 1 wherein E is trans—CH=CH—, $R_1$ is hydrogen, methyl, or ethyl, M is $H\overset{\frown}{O}H$, s is zero or one, T when present is chloro, fluoro, or trifluoromethyl, $R_8$ and $R_9$ are methyl, or $R_8$ is hydrogen and $R_9$ is fluoro, and $C_tH_{2t}$ is —$CH_2$— or —$CH_2CH_2$—, and pharmacologically acceptable salts thereof when $R_1$ is hydrogen.

4. cis-4,5-didehydro-17-phenyl-18,19,20-trinor-$PGF_{1\alpha}$, a compound according to claim 2 wherein $R_1$, $R_2$, $R_8$ and $R_9$ are hydrogen, s is zero, and $C_tH_{2t}$ is —$CH_2$—.

5. cis-4,5-didehydro-17-phenyl-18,19,20-trinor-$PGF_{1\alpha}$ methyl ester, a compound according to claim 2 wherein $R_1$ is methyl, $R_2$, $R_8$, and $R_9$ are hydrogen, s is zero, and $C_tH_{2t}$ is —$CH_2$—.

6. cis-4,5-didehydro-15-methyl-17-phenyl-18,19,20-trinor-$PGF_{1\alpha}$, a compound according to claim 2 wherein $R_1$, $R_8$, and $R_9$ are hydrogen, $R_2$ is methyl, s is zero, and $C_tH_{2t}$ is —$CH_2$—.

7. cis-4,5-didehydro-15-methyl-17-phenyl-18,19,20-trinor-$PGF_{1\alpha}$ methyl ester, a compound according to claim 2 wherein $R_1$ and $R_2$ are methyl, $R_8$ and $R_9$ are hydrogen, s is zero, and $C_tH_{2t}$ is —$CH_2$—.

* * * * *

UNITED STATES PATENT AND TRADEMARK OFFICE
CERTIFICATE OF CORRECTION

PATENT NO. : 4,032,561
DATED : June 28, 1977
INVENTOR(S) : Barney J. Magerlein

It is certified that error appears in the above-identified patent and that said Letters Patent are hereby corrected as shown below:

Column 1, line 46: " -above-mentioned 2CH-;" should read: -- $-CH_2CH_2-$; --.
Column 15, line 36: "o-, , or" should read: -- o-, m-, or --.
Column 17, line 10: "$PGB_x$" should read: -- $PGB_2$ --.
Column 24, line 29: "$PGF\alpha$-type" should read: -- $PGF\beta$-type --.
Column 24, line 60: "trans-CHxCH=CH-" should read: -- trans-CH=CH- --.
Column 29, lines 28-29: "trans-CH=$\lambda$ CH-" should read: -- trans-CH=CH- --.
Column 30, lines 8-9: "trans-CH=$\lambda$ CH-" should read: -- trans-CH=CH- --.
Column 30, line 32: "$_{ct}H_{2t}$" should read: -- $C_tH_{2t}$ --.

Signed and Sealed this

Sixth Day of June 1978

[SEAL]

Attest:

RUTH C. MASON
Attesting Officer

DONALD W. BANNER
Commissioner of Patents and Trademarks